United States Patent

Golden et al.

[11] Patent Number: 5,902,238
[45] Date of Patent: *May 11, 1999

[54] MEDICAL TUBE AND APPARATUS FOR LOCATING THE SAME IN THE BODY OF A PATIENT

[75] Inventors: Robert N. Golden, Kirkland; Fred E. Silverstein, Seattle, both of Wash.

[73] Assignee: University of Washington, Seattle, Wash.

[ * ] Notice: This patent issued on a continued prosecution application filed under 37 CFR 1.53(d), and is subject to the twenty year patent term provisions of 35 U.S.C. 154(a)(2).

[21] Appl. No.: 08/644,446

[22] Filed: May 2, 1996

Related U.S. Application Data

[63] Continuation-in-part of application No. 08/307,230, Sep. 14, 1994, Pat. No. 5,622,169, which is a continuation-in-part of application No. 08/121,929, Sep. 14, 1993, Pat. No. 5,425,382.

[51] Int. Cl.$^6$ ........................................................ A61B 5/06
[52] U.S. Cl. ............................................. 600/424; 128/899
[58] Field of Search ................................ 128/653.1, 654, 128/899; 600/407, 424, 899

[56] References Cited

U.S. PATENT DOCUMENTS

| | | | |
|---|---|---|---|
| 3,528,402 | 9/1970 | Abramowitz | 600/424 |
| 4,244,362 | 1/1981 | Anderson . | |
| 4,809,713 | 3/1989 | Grayzel | 607/122 |
| 5,134,370 | 7/1992 | Jefferts et al. | 324/247 |
| 5,257,636 | 11/1993 | White | 128/653.1 |
| 5,429,131 | 7/1995 | Scheinman et al. | 607/122 |
| 5,431,640 | 7/1995 | Gabriel | 600/12 |
| 5,624,430 | 4/1997 | Eton et al. | 128/772 |

OTHER PUBLICATIONS

Ram et al., "Heart Catheterization in a Neonate by Interacting Magnetic Fields: A New and Simple Method of Catheter Guidance", Catheterization and Cardiovascular Diagnosis 22:317–319, 1991.

*Primary Examiner*—William E. Kamm
*Assistant Examiner*—George R. Evanisko
*Attorney, Agent, or Firm*—Seed and Berry LLP

[57] ABSTRACT

A medical tube, apparatus and method for locating the medical tube within the body of a patient. The medical tube has a permanent magnet associated therewith and is capable of being located by a detection apparatus which senses the static magnetic field strength gradient generated by the magnet associated with the medical tube and indicates the value of the gradient to the user. In one embodiment, the magnet is associated with the distal end of the medical tube in a fixed orientation with a magnetic dipole pointing to the proximal end and parallel to a longitudinal axis of the medical tube such that polarity of the magnet's static magnetic field as sensed by the detection apparatus indicates the orientation of the distal end of the medical tube with the body of a patient.

8 Claims, 10 Drawing Sheets

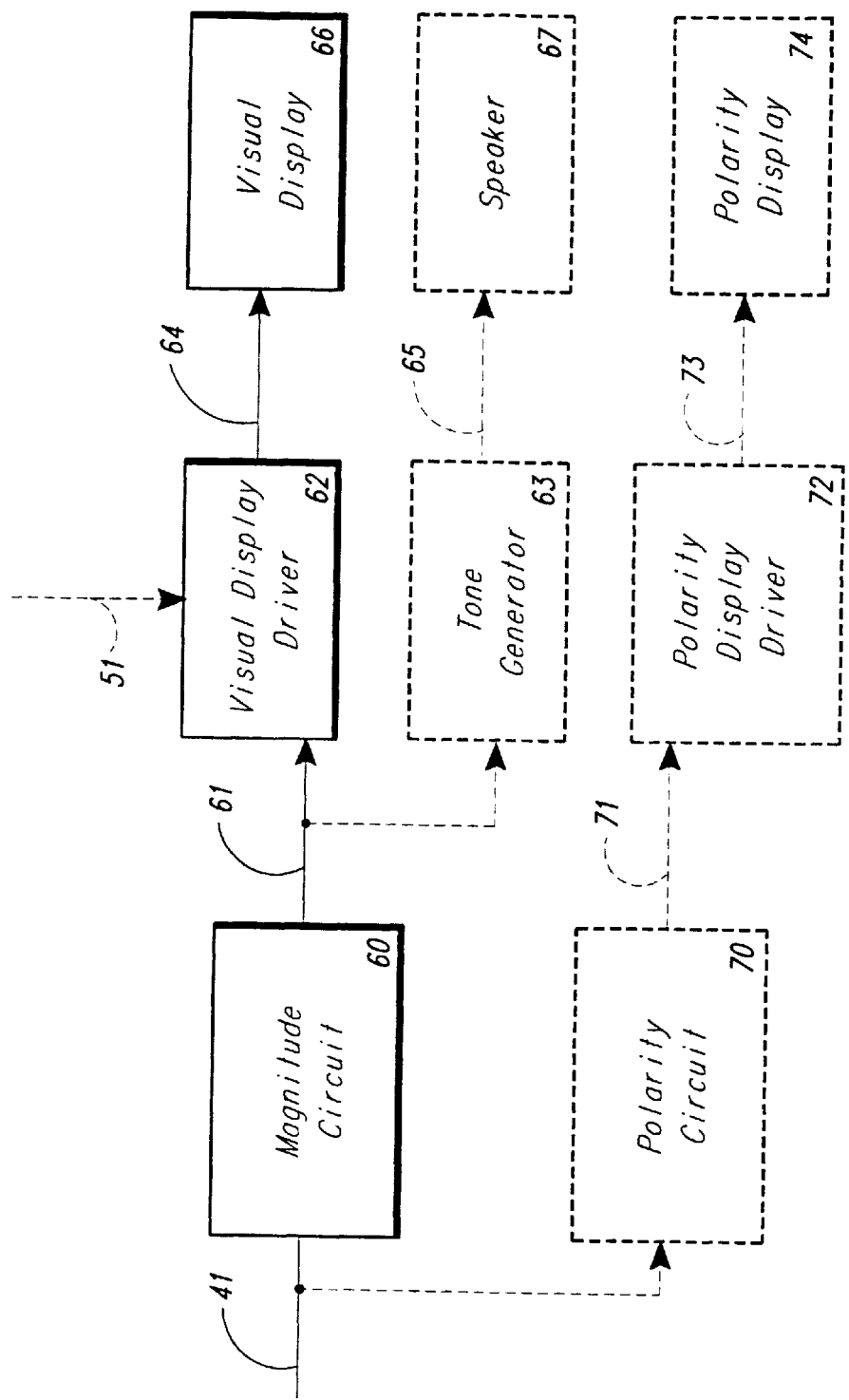

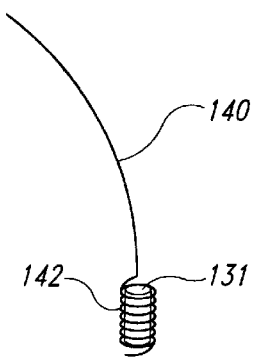
*Fig. 12A*
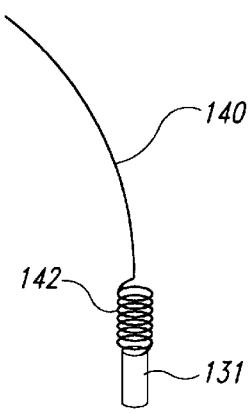
*Fig. 12B*
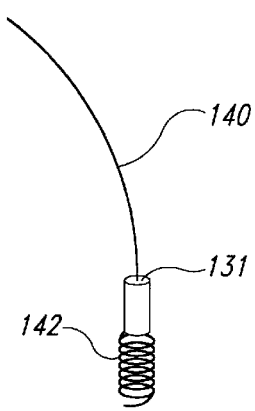
*Fig. 12C*
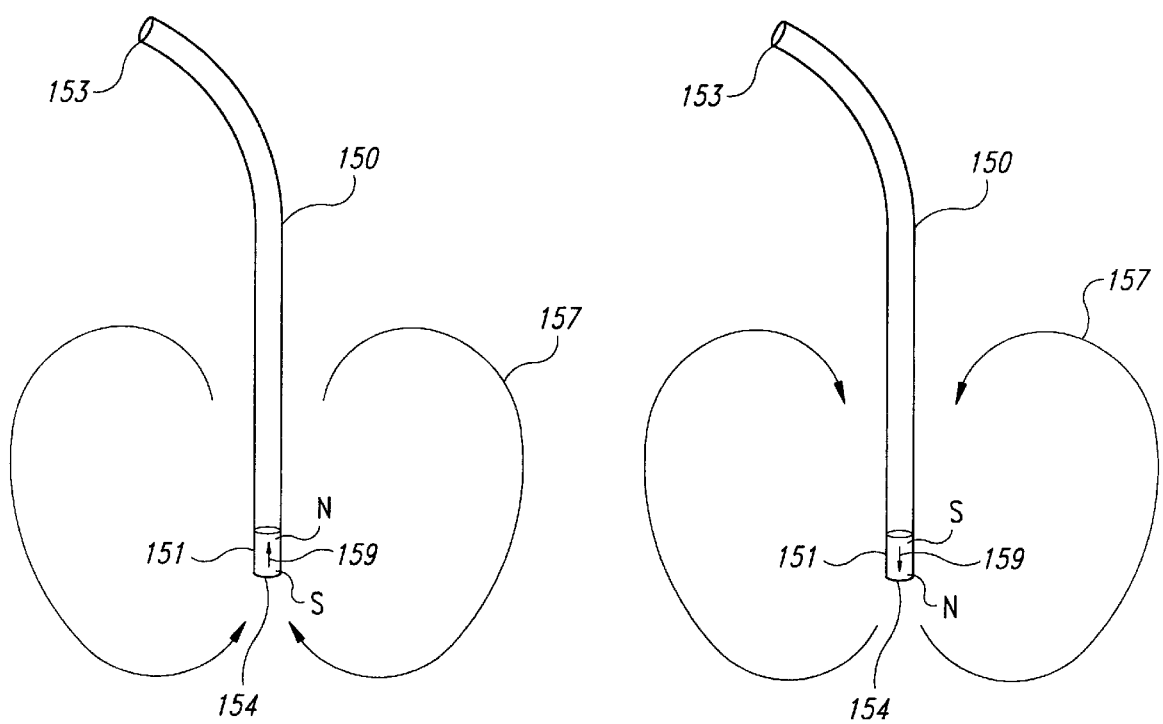
*Fig. 13A*    *Fig. 13B*

MEDICAL TUBE AND APPARATUS FOR LOCATING THE SAME IN THE BODY OF A PATIENT

CROSS-RELATED APPLICATIONS

This application is a continuation-in-part of U.S. application Ser. No. 08/307,230, filed Sep. 14, 1994 now U.S. Pat. No. 5,622,169; which is a continuation-in-part of U.S. application Ser. No. 08/121,929, filed Sep. 14, 1993, which issued as U.S. Pat. No. 5,425,382.

TECHNICAL FIELD

This invention is generally directed to a medical tube, apparatus and method for detecting the location of the medical tube within the body of a patient and, more specifically, to a medical tube capable of being located using a detection apparatus which senses a static magnetic field strength gradient generated by a magnet associated with the medical tube.

BACKGROUND OF THE INVENTION

There are many instances in clinical medicine where detecting the location of a medical tube within a patient is important. For example, when positioning feeding tubes through the mouth or nose of a patient, it is essential that the end of the feeding tube pass into the patient's stomach, and that it does not "curl up" and remain in the esophagus. If the end of the feeding tube is not properly positioned within the stomach, aspiration of the feeding solution into the patient's lungs may occur. In addition to feeding tubes, a variety of other medical tubes require accurate positioning within a patient's body, including dilating tubes to widen an esophageal stricture, tubes for measuring pressure waves in the stomach and esophagus of a patient who is suspected of having esophageal motor disorders, Sengstaken-Blakemore tubes in the stomach and esophagus of a patient to control bleeding from varicose veins in the esophagus, colonic decompression tubes in the colon of a patient to assist in relieving distention of the colon by gas, urologic tubes in the bladder, ureter or kidney of a patient, and vascular tubes in the heart or pulmonary arteries of a patient.

Currently, the location of a medical tube within the body of a patient is routinely detected by the use of imaging equipment, such as a chest or abdominal X-ray. However, such a procedure requires transportation of the patient to an X-ray facility or, conversely, transportation of the X-ray equipment to the patient. This is both inconvenient and costly to the patient, and is particularly stressful in those instances where the patient repeatedly and inadvertently removes a medical tube, such as a feeding tube, thus requiring repeated reinsertion and X-rays.

Prior attempts at detecting the location of medical tubes within a patient have met with only limited success. For example, in U.S. Pat. No. 5,099,845 to Besz et al., a transmitter is located within a catheter, and an external receiver, tuned to the frequency of the transmitter, is used to detect the location of the catheter within the patient. This approach, however, requires either an external or internal power source to drive the transmitter. An external power source adds significant risk associated with shock or electrocution, and requires that electrical connections be made prior to positioning of the catheter within the patient. An internal power source, such as a battery, must be relatively small and can only provide power to the transmitter for a limited time. This precludes long-term detection of the catheter's location, and poses additional risks associated with placing a battery internally in a patient, such as the risk of battery leakage or rupture. In addition, the transmitter is relatively complex, and requires an active electronic circuit (either internal or external to the catheter), as well as the various wires and connections necessary for its proper function. Lastly, the signal produced by the transmitter is attenuated differently by different body tissues and bone. This attenuation requires adjustments in the transmitter's signal strength and frequency depending on the location of the catheter within the patient's body.

A further attempt at detecting the location of medical tubes within a patient is disclosed in U.S. Pat. No. 4,809,713 to Grayzel. There, an electrical cardiac-pacing catheter is held in place against the inner heart wall of a patient by the attraction between a small magnet located in the tip of the pacing catheter and a large magnet located on (e.g., sewn into) the patient's chest wall. An indexed, gimbaled, three-dimensional compass is used to determine the best location for the large magnet. The compass' operation relies upon the torque generated by the magnetic forces between the small magnet and the magnetized compass pointer in order to point the compass towards the small magnet. However, this compass will simultaneously try to orient itself to the earth's ambient magnetic field. Because of this, the forces between the small magnet and the magnetized compass pointer at distances greater than several centimeters are not strong enough to accurately orient the compass towards the small magnet. Furthermore, although the compass aids positioning of the large magnet, positioning of the small magnet, and hence the pacing catheter, still requires the use of imaging equipment, such as X-ray or ultrasound.

For the foregoing reasons, there is a need in the art for a medical tube, apparatus and method for detecting the location of the medical tube within the body of a patient which avoids the problems inherent in existing techniques. The medical tube, apparatus and method should provide for the detection of the medical tube at distances ranging from several centimeters to several decimeters, should not require the medical tube to have an internal or external power source, and should obviate the need to independently verify positioning of the medical tube with imaging equipment.

SUMMARY OF THE INVENTION

Accordingly, it is an object of the present invention to provide a medical tube, apparatus and method for detecting the location of the medical tube within the body of an animal patient (including humans) without the aid of imaging equipment, particularly X-ray. It is a further object to detect the location of the medical tube without relying upon torque generated by the magnetic forces between the medical tube and the detection apparatus. Yet, a further object is to detect the location of the medical tube while dynamically nulling sensing of the earth's ambient magnetic field, and to thereby allow detection distances suitable for locating a wide variety of medical tubes at any location within the body of the patient.

The present invention satisfies these objectives by providing a medical tube, apparatus and method for detecting the location of a magnet associated with a medical tube within the body of a patient.

In one aspect of this invention, a medical tube is disclosed having a permanent magnet associated therewith. In one embodiment, the medical tube comprises a tube or device suitable for insertion into a patient's body and a permanent magnet associated with the medical tube, wherein the permanent magnet is associated with the medical tube in a manner such that it is magnetized parallel to a transverse axis of the medical tube.

In another embodiment, the medical tube is a Sengstaken-Blakemore tube comprising an esophageal balloon, a gastric balloon and a permanent magnet, wherein the permanent magnet is associated with the tube at a location between the esophageal balloon and gastric balloon.

In a further embodiment, the medical tube is a feeding tube comprising a tube and a permanent magnet associated therewith, wherein the permanent magnet is affixed to the end of a guide wire which is removably located within an interior volume of the tube.

In yet a further embodiment, a guide wire is disclosed comprising a wire sized to permit a tube to pass thereover and a permanent magnet associated with the end of the wire. In a preferred embodiment, the end of the guide wire comprises a spring, and the magnet is positioned within or affixed to the spring.

In still a further embodiment, the medical tube comprises a tube or device suitable for insertion into a patient's body and a permanent magnet associated with the medical tube, the medical tube having a proximal end and a distal end. The permanent magnet generates a static magnetic field of sufficient strength per unit volume to permit detection by a detection apparatus of the magnet's static magnetic field when the medical tube is inserted into the patient's body, the detection apparatus having at least two static magnetic field strength sensors configured geometrically to null detection of ambient homogeneous magnetic fields to a value of zero. In other words, the sensors allow gradiometric measurement of ambient magnet field gradients, and display a zero value in the presence of a homogeneous ambient field. The magnet is associated with the distal end of the medical tube in a fixed orientation with a magnetic dipole pointing to the proximal end and parallel to a longitudinal axis of the medical tube such that polarity of the magnet's static magnetic field as sensed by the detection apparatus indicates the orientation of the distal end of the medical tube within the patient's body.

In another aspect of this invention, the apparatus of this invention comprises a first and second means for sensing a first and second static magnetic field strength, respectively, at first and second distances from the magnet, respectively, where the second distance is greater than the first; means for providing a first detection signal, which is a function of the first static magnetic field strength; means for providing a second detection signal, which is a function of the second static magnetic field strength; means for providing a differential signal, which is a function of the difference between the first and second detection signals; and means for indicating a value for the differential signal. The first and second detection signals and the differential signal can be scalars or vectors.

The first and second sensing means also provide, respectively, a first sensor signal, which is a function of the first static magnetic field strength, and a second sensor signal, which is a function of the second static magnetic field strength. The means for providing the first detection signal receives the first sensor signal, and the means for providing the second detection signal receives the second sensor signal. Finally, the means for providing the differential signal receives the first and second detection signals, and the means for indicating the differential signal's value receives the differential signal. The first and second sensor signals can be scalars or vectors.

By sensing the static magnetic field strength of the magnet associated with the medical tube, the present invention obviates the need for imaging equipment, such as X-ray, to verify positioning of the medical tube. Also, by sensing the magnet's field strength at two different distances (i.e., the first and second distances) from the magnet between which the magnet's field strength will have a gradient and the earth's field strength will not, and by indicating the gradient to the user, the present invention dynamically nulls sensing of the earth's ambient magnetic field. This nulling allows the magnet to be sensed at distances ranging from several centimeters to several decimeters, which makes the detection apparatus suitable for locating the medical tube at any location within the patient's body.

In one embodiment of this invention, the first and second sensing means comprise a static magnetic field strength sensor driver, and first and second static magnetic field strength sensors. The driver provides a driver signal which causes the sensors to provide the first and second sensor signals. In a preferred embodiment, the driver comprises an oscillator and output transistors, wherein the output transistors are alternately switched by the oscillator and are thereby caused to provide the driver signal. The sensors each comprise a flux-gate toroidal sensor, which includes an excitation winding which receives a driver signal, and a detection winding which provides the respective sensor signal. By providing a driver signal which causes the sensors to provide the first and second sensor signals, the present invention does not need to rely upon magnetic forces between the magnet and the apparatus for detecting the location of the medical tube.

In another embodiment, the detection apparatus further comprises a means for automatically controlling, monitoring, and calibrating (a) the first and second means for sensing the first and second static magnetic field strengths; (b) the means for providing the first detection signal; (c) the means for providing the second detection signal; (d) the means for providing the differential signal; and (e) the means for indicating the differential signal's value. In a preferred embodiment, the automatic controlling, monitoring, and calibrating means is a microprocessor.

In another aspect of this invention, the apparatus of this invention comprises the static magnetic field strength sensor driver, the first and second static magnetic field strength sensors, first and second amplifiers, first and second integrators, a differential amplifier, a magnitude circuit, a visual display driver, and a visual display.

The first amplifier receives the first sensor signal and provides a first amplified signal which is proportional to the first sensor signal. Similarly, the second amplifier receives the second sensor signal and provides a second amplified signal which is proportional to the first sensor signal. The first and second amplified signals can be scalars or vectors.

The first and second integrators receive the first and second amplified signals, respectively, and provide the first and second detection signals, respectively. The differential amplifier receives the first and second detection signals and provides the differential signal.

Further, the magnitude circuit receives the differential signal and provides a magnitude signal which is proportional to the magnitude of the differential signal. The visual display driver receives the magnitude signal and provides a visual display signal. The visual display receives and visually indicates the visual display signal.

In a preferred embodiment, the visual display driver comprises a light emitting diode bar array driver, and the visual display comprises a light emitting diode bar array.

In another preferred embodiment, the apparatus further comprises a tone generator for receiving the magnitude signal and providing a tone signal which is a function of the magnitude signal, and a speaker for receiving and audibly indicating the tone signal.

In still another preferred embodiment, the apparatus further comprises a polarity circuit for receiving the differential signal and providing a polarity signal which is a function of the polarity of the differential signal, a polarity display driver for receiving the polarity signal and providing a polarity display signal, and a polarity display for receiving and visually indicating the polarity display signal.

In still another preferred embodiment, the apparatus further comprises the microprocessor for automatically controlling, monitoring and calibrating the static magnetic field strength sensor driver, the first amplifier, the second amplifier, the differential amplifier and the visual display driver.

In a further aspect of this invention, the detection apparatus comprises the first and second static magnetic field strength sensors, first and second detectors, a microprocessor, a magnitude circuit, and an indicator. In this embodiment, the first and second sensor signals, the first and second detection signals, and the differential signal are vectors.

The first detector receives the first sensor signal and provides the first detection signal which is a function of the first sensor signal. Similarly, the second detector receives the second sensor signal and provides the second detection signal which is a function of the second sensor signal. The microprocessor receives the first and second detection signals and provides the differential signal which is a function of the difference between the first and second detection signals.

In a preferred embodiment, the first sensor includes x, y, and z-axis oscillators which provide x, y, and z components, respectively, of the first sensor signal. Each oscillator of the first sensor has an associated wound-core inductive sensor. The x, y, and z components are functions of the inductance of the inductive sensor of the components' respective oscillators, and the inductance is a function of the first static magnetic field strength. Likewise, the second sensor includes x, y, and z-axis oscillators which provide x, y, and z components, respectively, of the second sensor signal, and each oscillator of the second sensor has an associated wound-core inductive sensor. The x, y, and z components are functions of the inductance of the inductive sensor of the components' respective oscillators, and the inductance is a function of the second static magnetic field strength.

In a further preferred embodiment, the first detector includes x, y, and z-axis frequency counters which receive the x, y, and z components, respectively, of the first sensor signal, and provide x, y, and z components of the first detection signal. Similarly, the second detector includes x, y, and z-axis frequency counters which receive the x, y, and z components, respectively, of the second sensor signal, and provide x, y, and z components of the second detection signal.

In still another aspect of this invention, a method for detecting the location of a magnet associated with a medical tube within the body of a patient comprises the following steps: sensing the first and second static magnetic field strengths at the first and second distances; providing the first and second sensor signals; receiving the first and second sensor signals and providing the differential signal; receiving and indicating the value of the differential signal; and determining the location of the medical tube by varying the first and second distances until the greatest value is indicated.

In a preferred embodiment, providing the first sensor signal includes tuning x, y, and z-axis oscillators each with the inductance of their associated wound-core inductive sensor. The inductance is a function of the sensed first field strength, and further includes providing x, y, and z components of the first sensor signal from the x, y, and z-axis oscillators, respectively. Likewise, providing the second sensor signal includes tuning x, y, and z-axis oscillators each with the inductance of their associated wound-core inductive sensor. The inductance is a function of the sensed second field strength, and further includes providing x, y, and z components of the second sensor signal from the x, y, and z-axis oscillators, respectively.

In a further preferred embodiment, receiving the first and second sensor signals and providing the differential signal includes determining the respective frequencies of the x, y, and z components of the first and second sensor signals. It further includes determining the differences between the first sensor signal x, y, and z component frequencies and the corresponding second sensor signal x, y, and z component frequencies, and then providing the differential signal equal to the magnitude and polarity of the differences.

In still another aspect of this invention, a method of verifying the location of a magnet associated with the end of a medical tube within the body of a patient comprises the following steps: sensing the first and second static magnetic field strengths at the first and second distances; providing the first and second sensor signals; receiving the first and second sensor signals and providing the differential signal; receiving and indicating the polarity of the differential signal; and manipulating the magnet until the indicated polarity changes.

These and other features of the present invention will be better understood with reference to the following detailed description, appended claims and accompanying drawings.

BRIEF DESCRIPTION OF THE DRAWINGS

FIGS. 1A and 1B are block diagrams illustrating the structure and operation of a representative detection apparatus of this invention.

FIG. 12 illustrates a guide wire having a spring located at the distal end thereof, and wherein a magnet is located within the spring (FIG. 12A) or affixed to either end of the spring (FIGS. 12B and 12C).

FIG. 13 illustrates in greater detail the static magnetic field strength of a magnet associated with a medical tube of this invention. Specifically the direction of the sensed dipole (i.e., polarity) depends on the orientation of the magnet: magnet dipole pointing to the proximal end—FIG. 13A; magnetic dipole pointing to the distal end—FIG. 13B.

DETAILED DESCRIPTION OF THE INVENTION

Figure 1A:
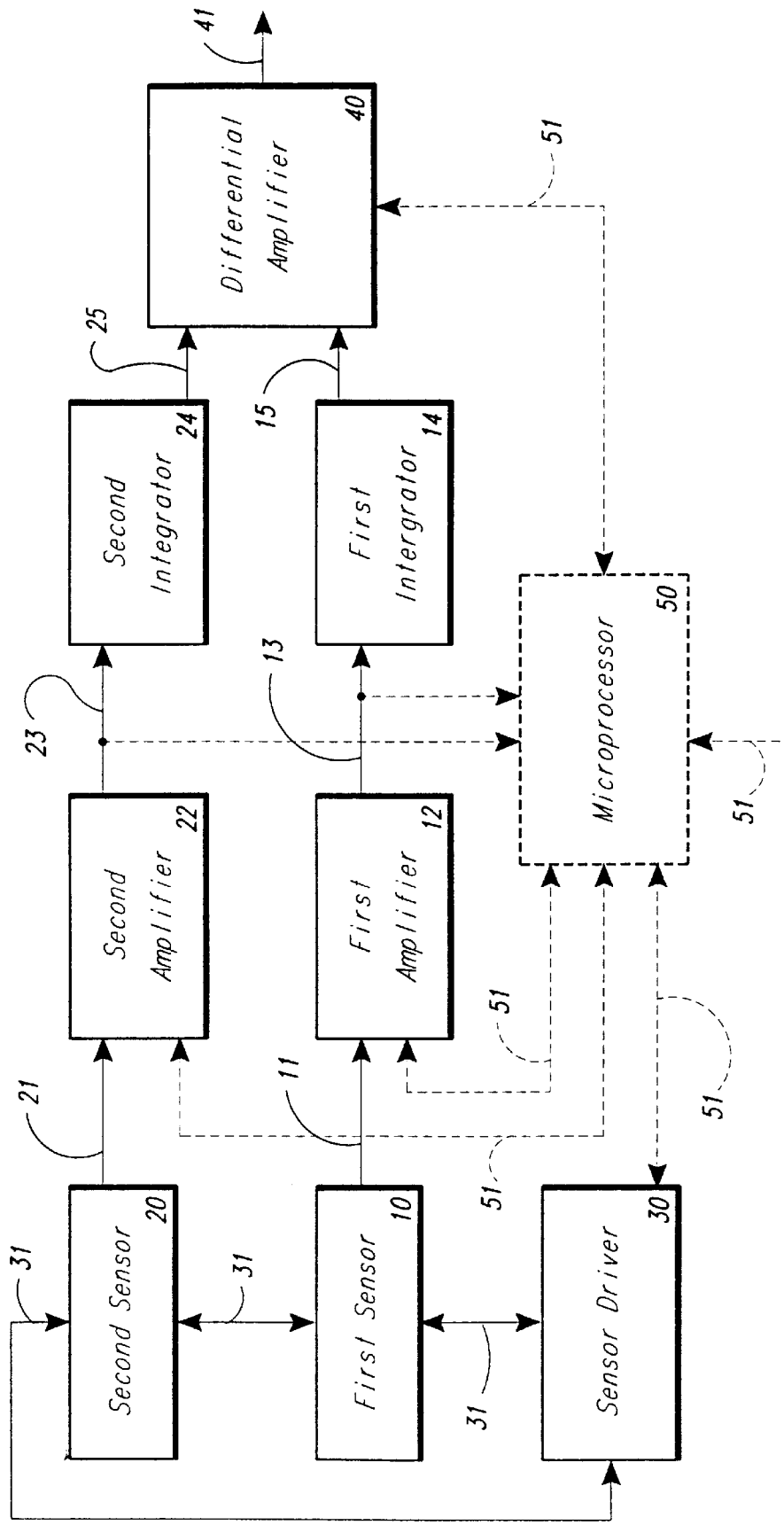

The present invention provides a medical tube, apparatus and method for detecting the location of the medical tube within the body of a patient. As used herein, the term "medical tube" means any type of tube or device which may be inserted into a patient's body, including (but not limited to) catheters, guide wires, and medical instruments. For example, catheters include such items as feeding tubes, urinary catheters, guide wires and dilating catheters, as well as nasogastric tubes, endotracheal tubes, stomach pump tubes, wound drain tubes, rectal tubes, vascular tubes, Sengstaken-Blakemore tubes, colonic decompression tubes, pH catheters, motility catheters, and urological tubes. Guide wires are often used to guide or place dilators and other medical tubes. Medical instruments include endoscopes and colonoscopes. In short, the location of any foreign object within a patient's body is a suitable device for detection by the present invention, and is encompassed within the term "medical tube."

The present invention detects the location of the medical tube by sensing the static magnetic field strength gradient produced by a permanent magnet associated with the medical tube. As used herein, the term "associated with" means permanently fixed, removably attached, or in close proximity to, the medical tube. In one embodiment, such as a feeding tube, the magnet is associated with the end of the medical tube. In another embodiment, such as a Sengstaken-Blakemore tube, the magnet is associated with the medical tube at a location above the gastric balloon. Preferably, the magnet is a small, cylindrical, rotatably attached, rare-earth magnet. Suitable magnets include rare earth magnets such as samarium cobalt and neodymium iron boron, both of which generate high field strengths per unit volume. While magnets which generate a high field strength for their size are preferred, weaker magnets such as Alnico or ceramic may also be utilized.

Since the magnet of this invention is permanent, it requires no power source. Accordingly, the magnet maintains its magnetic field indefinitely, which allows long-term positioning and detection of medical tubes without the disadvantages associated with an internal or external power source. In particular, by avoiding the use of a power source, the undesirable electrical connections necessary for the use of a power source are avoided. Thus, there is no risk of shock to (or possible electrocution of) the patient. Furthermore, the magnet's static magnetic field passes unattenuated through body tissue and bone. This property allows the use of the present invention to detect the medical tube at any location within the patient's body.

The magnet, and hence the medical tube, is detected using a detection apparatus which contains at least two static magnetic field strength sensors configured geometrically to null detection of ambient, homogeneous magnetic fields (e.g., the earth's field), while still detecting the magnetic field strength gradient produced by the magnet. The detection apparatus is an active, electronic instrument, and can detect the relatively small magnetic field strength gradient produced by the magnet at distances ranging from several centimeters to several decimeters, and preferably from about 2 centimeters to about 3 decimeters. It also indicates the value of the gradient, thus allowing the user to accurately determine the location of the magnet, and hence the medical tube. In a preferred embodiment, the detection apparatus indicates the value of the gradient as both a magnitude and a polarity. By manipulating the magnet until the indicated polarity changes, detection of the location of the medical tube can be verified. Such manipulation of the magnet can be accomplished either by means of an attached guide wire, or by rotating the medical tube itself.

The static magnetic field strength sensors can detect the field strength as a scalar or, in a preferred embodiment, as a vector. In this preferred embodiment, the sensors each detect separate strength values in the orthogonal x, y, and z axes.

Due to the sensitivity of the apparatus of the present invention to the magnet's field strength gradient, additional imaging equipment is not necessary to detect the location of the medical tube. Accordingly, the present invention is suitable for use in environments which lack such equipment. For example, nursing homes rarely have X-ray equipment on-site, and the apparatus and method of the present invention is particularly suited for use in such facilities.

Referring to FIGS. 1A and 1B, a block diagram illustrating the structure and operation of a representative detection apparatus of this invention is shown. In FIG. 1A, a static magnetic field strength sensor driver (30) provides a first static magnetic field strength sensor (10) and a second static magnetic field strength sensor (20) with a driver signal (31), thereby causing the first sensor (10) to provide a first sensor signal (11) and the second sensor (20) to provide a second sensor signal (21).

The first and second sensor signals (11) and (21) are functions of a first and second static magnetic field strength, respectively, sensed at a first and second distance, respectively, from the magnet. The first sensor (10) and the second sensor (20) are separated by a distance equal to the difference between the first and second distances. In this geometric configuration, while an ambient magnetic field strength (such as the earth's field strength) will have an equivalent value when sensed by either sensor (10) or (20), the magnet's magnetic field strength will have a different value depending on whether it is sensed by the first sensor (10) or the second sensor (20). By subtracting the field strength sensed at one sensor from the field strength sensed at the other, the magnet's field strength gradient can be sensed while at the same time nulling sensing of the earth's field strength. Several different types of sensors may be used in the practice of this invention, including (but not limited to) Hall-effect, flux-gate, wound-core inductive, squid, magneto-resistive, and nuclear precession sensors. In addition, a plurality of sensors may be employed.

In a preferred embodiment, the first sensor (10) and the second sensor (20) detect the first and second static magnetic field strengths, respectively, as vectors. In this embodiment the first and second sensor signals (11) and (21) are also vectors. This embodiment is discussed in more detail below with reference to FIGS. 5 and 6.

A first amplifier (12) receives the first sensor signal (11) and provides a first amplified signal (13) which is proportional to the first sensor signal (11). Similarly, a second amplifier (22) receives the second sensor signal (21) and provides a second amplified signal (23) which is proportional to the second sensor signal (21). In a preferred embodiment, the proportionality constant between the amplified signals (13) and (23) and the sensor signals (11) and (21) (i.e., the gain of the amplifiers (12) and (22)) will be variable, either automatically or manually, to maintain appropriate sensitivity as the detection apparatus approaches the magnet. In the preferred embodiment, the amplified signals (13) and (23) are vectors.

A first integrator (14) receives the first amplified signal (13) and provides a first detection signal (15), which is the integral of the first amplified signal (13). Likewise, a second integrator (24) receives the second amplified signal (23) and provides a second detection signal (25), which is the integral of the second amplified signal (23). Because the integrals of the amplified signals (13) and (23), and hence the sensor signals (11) and (21), are proportional to the sensed first and second field strengths, the detection signals (15) and (25) are proportional to the sensed first and second field strengths. In a preferred embodiment, the detection signals (15) and (25) are vectors.

A differential amplifier (40) receives the detection signals (15) and (25) and provides a differential signal (41) which is a function of the difference between the detection signals (15) and (25). In the absence of any sensed magnetic field strength gradient, the differential signal (41) from the differential amplifier (40) has a value of zero. When the detection apparatus is brought in close proximity to the magnet, the sensed value of the gradient between the sensors (10) and (20) is non-zero, and therefore the value of the differential signal (41) is non-zero. The polarity of the value (i.e., positive or negative) depends upon the orientation of the sensed magnet. In a preferred embodiment, the differential signal (41) is a vector, and the value of the differential signal includes the vector's magnitude and direction. This aspect of the present invention is discussed in greater detail below in reference to FIGS. 13 and 14.

Referring to FIG. 1B, a magnitude circuit (60) receives the differential signal (41) and provides a magnitude signal (61) which is proportional to the magnitude of the differential signal (41). A visual display driver (62) then receives the magnitude signal (61) and provides visual display signals (64) to a visual display (66). In a preferred embodiment, the visual display (66) displays a continuous analog representation of the magnet's magnetic field strength gradient, including its magnitude and polarity. Such a representation can be made with a light-emitting diode bar array or a liquid crystal display. In addition, a speaker (67) may optionally be employed. A tone generator (63) receives the magnitude signal (61) and provides a tone signal (65) to the speaker (67). The tone signal (65) is a function of the magnitude signal (61). The sound projected by the speaker (67) may change in volume or pitch corresponding to the magnitude signal (61). Such a visual display (66) and/or speaker (67) allows the user to move or sweep the detection apparatus over the patient's body and to quickly determine the nearest external point to the location of the internal magnet associated with the medical tube.

In a further embodiment, an optional polarity circuit (70) receives the differential signal (41) and provides a polarity signal (71) which is a function of the polarity of the differential signal (41). In a preferred embodiment, the differential signal (41) is a vector, and the polarity of the differential signal is the direction of the vector. A polarity display driver (72) then receives the polarity signal (71) and provides a polarity display signal (73) to a polarity display (74). In this embodiment, the magnet is preferably made of neodymium iron boron (NdFeB), and is a small cylinder with dimensions on the order of 0.10 inches in diameter and 0.25 to 0.5 inches in length. The magnet is magnetized parallel to the diameter or transverse axis—that is, the north and south magnetic poles are half cylinders.

This form of magnetization provides the greatest field strength at a given distance for such a cylindrical magnet. In addition, this magnet configuration allows the user to verify that the detection apparatus is sensing the magnet. Specifically, the user can rotate the magnet by, for example, manually rotating the medical tube. Such rotation about the longitudinal axis causes the sensed polarity to change. This change is indicated by the detection apparatus to the user. Alternatively, rather than rotating the medical tube, the magnet may be rotatably fixed to the medical tube such that the user may rotate the magnet by, for example, rotating a guide wire running down the medical tube and attached to the magnet.

Figure 8:
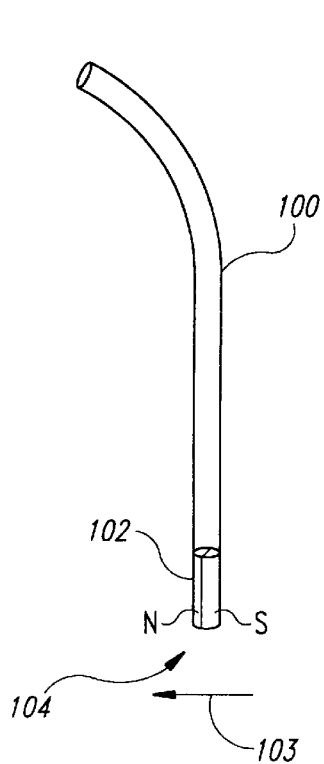
FIG. 8 illustrates a representative medical tube of this invention wherein the magnet is associated with the medical tube such that it is magnetized parallel to a transverse axis of the medical tube.
Figure 9:
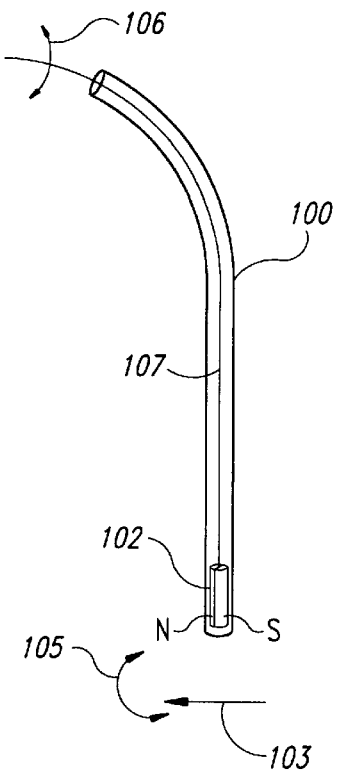
FIG. 9 illustrates a medical tube wherein the magnet is rotatably affixed to the medical tube.

This aspect of the invention is illustrated in FIGS. 8 and 9. Referring to FIG. 8, medical tube (100) has magnet (102) permanently affixed to the distal end (104) of the medical tube. Magnet (102) is magnetized parallel to the transverse axis of the tube, such that its dipole, as represented by arrow (103), is parallel to the transverse axis of the medical tube. Referring to FIG. 9, medical tube (100) has a magnet (102) attached to guide wire (107). By rotation of the guide wire as indicated by arrow (106), the magnet (which is magnetized such that its dipole, represented by arrow (103), is parallel to the transverse axis) is rotated around the longitudinal axis of the tube, thus rotating the dipole as indicated by arrow (105).

Referring to FIGS. 1A and 1B, an optional microprocessor (50) receives the amplified signals (13) and (23), and receives and provides control, monitoring, and calibration signals (51) from and to the sensor driver (30), the first and second amplifiers (12) and (22), the differential amplifier (40), and the visual display driver (62). It should be understood that the microprocessor (50) and its accompanying software may be the only digital element of an otherwise analog embodiment of the present invention, it may be an element in a mixed-mode embodiment, or it may be a digital element in a fully digital embodiment.

Figure 10:
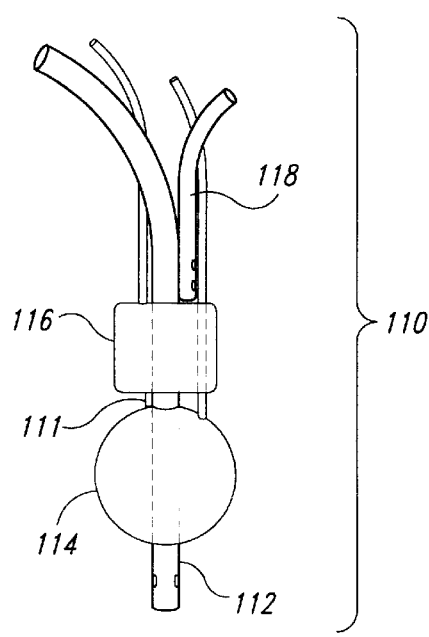
FIG. 10 illustrates a Sengstaken-Blakemore tube of this invention, wherein the magnet is associated with the tube between the esophageal and gastric balloons.

The apparatus of the present invention can detect the location of a wide variety of medical tubes. For example, as illustrated in FIG. 10, a Sengstaken-Blakemore tube (110) is sometimes inserted into the stomach and esophagus of a patient to stop bleeding from severe esophageal varices. Such a tube is a multilumen tube with a suction tube (112) in the stomach to detect bleeding, a gastric balloon (114) in the proximal stomach to act as an anchor to hold the tube in place and to press on varices at the junction between the esophagus and stomach, an esophageal balloon (116) to press on the varices directly and stop the bleeding, and a suction tube (118) above the esophageal balloon to remove saliva and blood. By placing a magnet (111) between the esophageal and gastric balloons, the present invention may be used to detect the magnet, and hence the position of the medical tube within the patient. With existing technology, it is generally necessary to wait 20–30 minutes in order to obtain an x-ray to confirm the location of the gastric balloon.

In the practice of this invention, once the magnet located on the tube between the esophageal and gastric balloons has been located in the stomach, the gastric balloon can be immediately inflated, thus substantially reducing the time and expense associated with existing x-ray localization of Sengstaken-Blakemore tubes.

Figure 11:
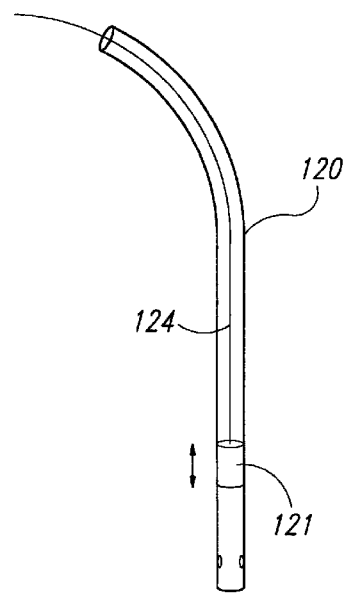
FIG. 11 illustrates a feeding tube comprising a tube and a magnet associated therewith, wherein the magnet is affixed to the end of a guide wire which is removably located within an interior volume of the tube.

In a further embodiment with respect to feeding tubes, the magnet may be incorporated into the tip of the tube. The weight of the magnet thus helps the tube be passed and advanced down the trachea and esophagus and into the stomach. In this embodiment, the size of the magnet should not exceed about 4–5 mm in diameter so that it can be passed into the stomach via either the nose or mouth. Once in place, the location of the magnet, and thus the end of the feeding tube, can be determined by the apparatus of the present invention. In an alternative embodiment, as illustrated in FIG. 11, the magnet (121) may be located at the end of a wire (124). The magnet is then inserted into the feeding tube (120) and pushed to the end of the tube by the wire. The feeding tube is then passed via the mouth or nose into the stomach. After the end of the feeding tube has been located at the desired position (i.e., by detection of the magnet at the end of the tube), the wire with the magnet attached is withdrawn from the feeding tube and either disposed of or sterilized. If a patient has a feeding tube placed every day, the same wire with magnet on the tip can be repeatedly used to locate the end of the feeding tube by the apparatus of this invention. Such a wire also serves to stiffen the feeding tube, making it easier to pass and advance.

Similarly, for several procedures in gastroenterology and other specialties, it is necessary to pass a guide wire into an organ. Once the guide wire is in place (usually with the assistance of an endoscope), another tube is passed over the guide wire. An example is esophageal stricture management. In this instance, there is a narrowing of the esophagus, and patients complain of trouble swallowing (dysphagia). A common technique used to dilate the stricture is to place a wire through the stricture and into the stomach, and then pass progressively larger dilators over the wire. The wire thus acts like a monorail or guide to keep the tip of the larger dilator catheter in the lumen. This reduces the chance of causing a perforation or hole in the esophagus. To ensure that the tip of the guide wire is in the stomach, x-ray verification is normally utilized.

In the practice of this invention, the location of such a guide wire may be confirmed by placing a magnet at or near the end of the guide wire. With regard to such esophageal stricture guide wires, the wire must be relatively stiff. Thus, as illustrated in FIG. 12, a spring (142) is normally located on the distal end of the wire (140) in order to avoid perforating the esophagus, and the spring is sized such that it can pass down the channel of an endoscope (typically 2.5 to 3.5 mm in diameter). Thus, a small magnet (131) may be located either above (FIG. 12C), below (FIG. 12B) or within (FIG. 12A) the spring of such guide wires. The guide wire and spring may then be inserted into the patient by passage down the channel of the endoscope. The present invention permits a physician to confirm that the tip of the guide wire remains in the stomach after the use of each progressively larger dilator.

This invention also permits the use of a guide wire having a spring tip/magnet end without the need for endoscope placement. Rather, the guide wire may be passed directly into the stomach, and its location determined by the apparatus of this invention. The size limitations associated with the use of an endoscope (i.e., the 2.5–3.5 mm diameter channel) can thus be avoided, and larger guide wires or tubes having magnets located near the end can be employed. For example, a flexible tube of about 8 mm in diameter having a magnet located at the end can readily be passed into the stomach, and larger dilators passed over the flexible tube. In this embodiment, the need for a spring is obviated due to the use of the larger diameter flexible tube rather than the guide wire.

As a medical tube is inserted into a patient, the location of the magnet can be sensed by moving the detection apparatus over the surface of the patient's body and watching the visual display. As the sensors approach the magnet inside the patient, the display will indicate a greater magnitude, by increasing the height of the display bar graph, and by increasing the volume or pitch of the sound projected by the speaker. Also, after initial tube positioning, the location of the magnet can be similarly verified at any time. Furthermore, by monitoring variations in the static magnetic field arising from motion of the magnet fixed, removably attached, or in close proximity to the medical tube, such as rocking or displacement due to the distinct frequencies of endogenous contractions between stomach and proximal small bowel, the location of the magnet which is fixed, removably attached, or in close proximity to the medical tube can be distinguished between the stomach and proximal small bowel.

As discussed above, the polarity of the value of the differential signal (i.e., positive or negative) depends on the orientation of the sensed magnet. As illustrated in FIG. 13, medical tube (150) having a proximal end (153) and distal end (154), has magnet (151) associated with the distal end of the tube. Lines (157) represent the static magnetic field produced by the magnet, the direction of which depends on whether the magnet is associated with the tube such that it's dipole, represented by arrow (159), points parallel to the longitudinal axis of the tube in the direction of the proximal end (FIG. 13A) or in the direction of the distal end (FIG. 13B).

Since the value of the differential signal indicates the direction of the magnet, the dipole of the magnet is associated with the medical tube in a fixed and known orientation. The medical tubes of this invention have the magnet affixed thereto as represented in FIG. 13A—that is, with the magnet's dipole pointing parallel to the longitudinal axis of the medical tube in the direction of the proximal end. By maintaining this orientation, the detection apparatus can indicate the orientation of the magnet. This feature of the present invention is useful in a variety of settings. For example, when placed at the end of a feeding tube, the apparatus indicates to the user whether the distal end of the feeding tube is pointing towards the patient's feet, or towards the patient's head. If pointing towards the patient's head, this could indicate that the tube is improperly inserted. Similarly, in the case of guide wires, the user can determine in which direction the guide wire is traveling to confirm that it has, for example, entered the desired artery and is traveling in the desired direction.

Figure 14A:
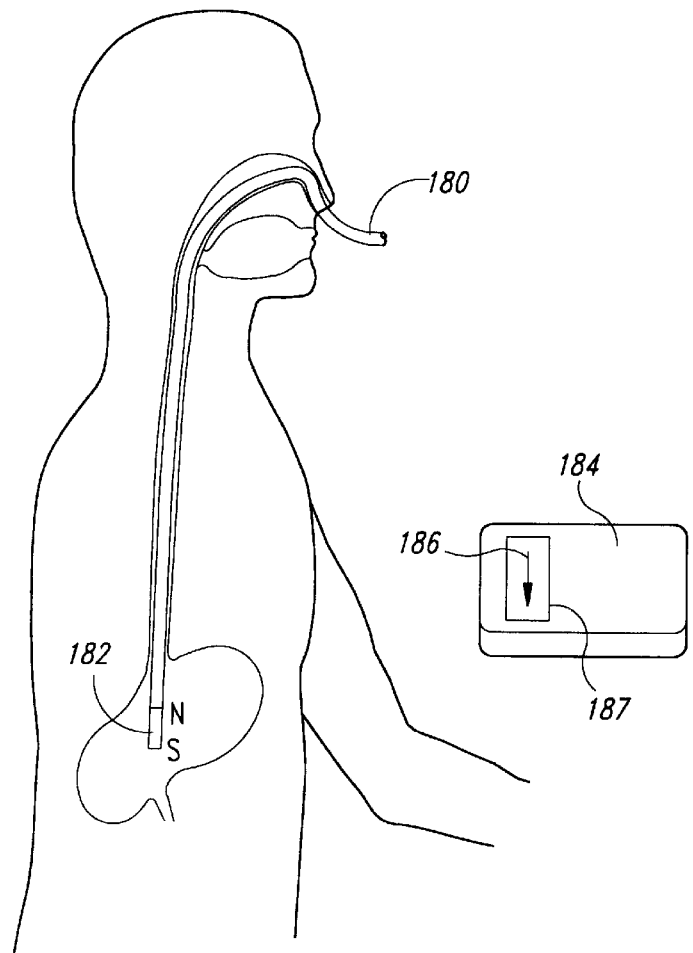
FIG. 14 illustrates detecting the location and orientation of a medical tube using the detection apparatus of this invention.
Figure 14B:
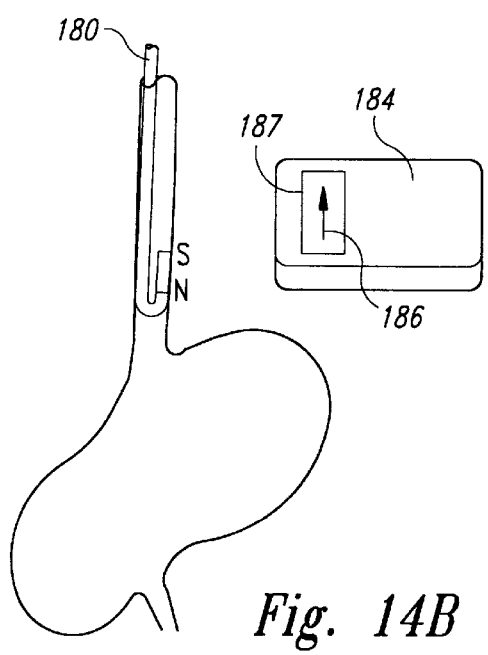

This aspect of the present invention is further illustrated by reference to FIGS. 14A and 14B. FIG. 14A depicts a feeding tube (180), with permanent magnet (182) associated with the distal end of the medical tube, and wherein the magnetic dipole of the magnet points toward the proximal end of the medical tube. After insertion into the patient's stomach, detection apparatus (184) detects the location of the magnet and, as indicated by arrow (186) in visual display (187), indicates to the user the orientation of the magnet, and hence the orientation of the distal end of the medical tube. For example, had feeding tube (180) "curled up" in the esophagus as illustrated in FIG. 14B, arrow (186) in visual display (187) of detection apparatus (184) would indicate that the distal end of the medical tube is pointing toward the patient's head, and thus the feeding tube is not correctly positioned within the patient.

Although the present invention has been described in detail, with reference to certain preferred embodiments, other embodiments are possible. For example, one skilled in this art would understand that the invention may be implemented with analog, mixed-mode, or digital elements, and with either discrete components or integrated circuits, or both. Furthermore, the following specific examples are offered by way of illustration, not limitation.

EXAMPLES

Example 1

Detection Apparatus

In this representative embodiment, the detection apparatus includes a pair of flux-gate toroidal sensors, their sensor driver, amplifiers, integrators, a differential amplifier, a magnitude circuit, a visual display driver, a visual display, a tone generator, a speaker, a polarity circuit, a polarity display driver, and a polarity display.

Figure 3:
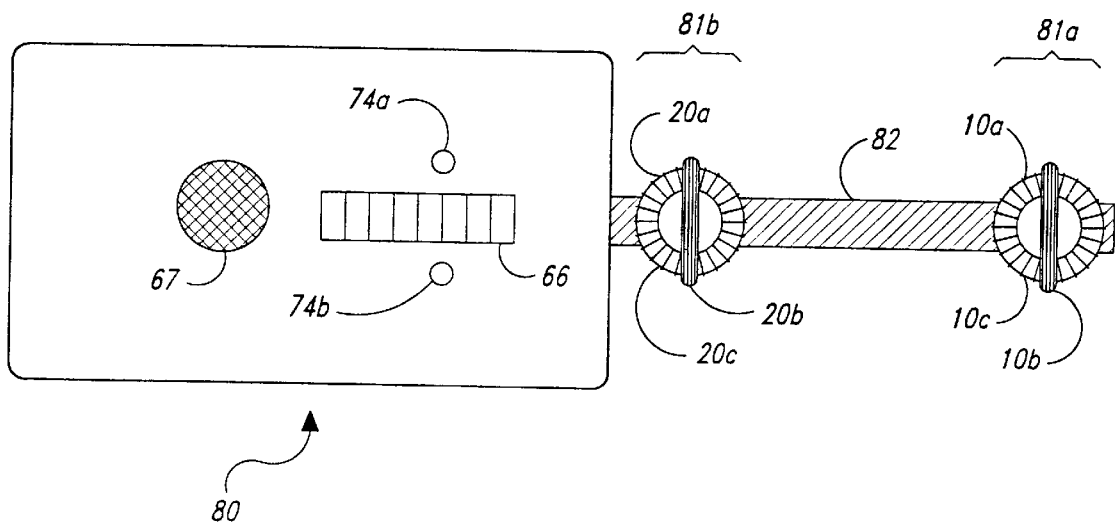
FIG. 3 illustrates an embodiment of a detection apparatus of this invention.

Referring to FIG. 3, each flux-gate toroidal sensor (81a) and (81b) comprises a 1 cm nickel-iron alloy toroid (10a) and (20a) with an excitation winding (10c) and (20c) and a detection winding (10b) and (20b). The excitation windings (10c) and (20c) are #37 gauge wire evenly wound in a toroidal manner around the perimeter of each toroid (10a) and (20a) such that the wire is closely spaced in a single layer. The detection windings (10b) and (20b) consist of #37 gauge wire closely wound around an outside diameter of each toroid (10a) and (20a). The flux-gate toroidal sensors (81a) and (81b) are fixed near each end of an 8 cm mounting arm (82), with their detection winding axes aligned and parallel to the length of the mounting arm.

Figure 2:
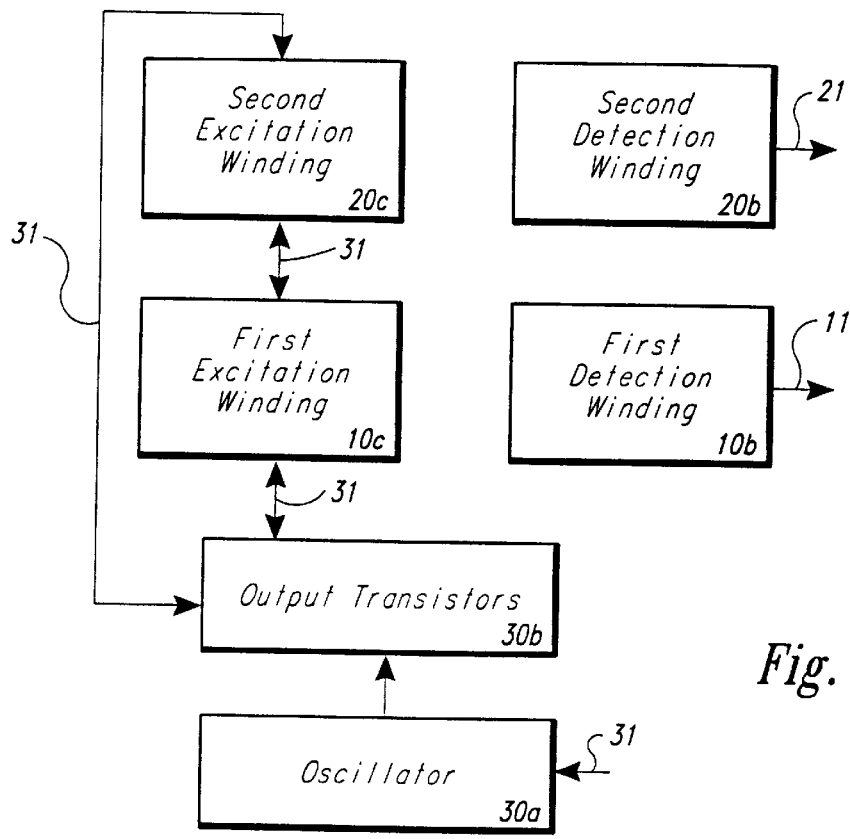
FIG. 2 is a block diagram illustrating an embodiment of the first and second sensor, as well as the sensor driver.

Referring to FIGS. 1 through 3, the sensor driver (30) for each flux-gate toroidal sensor (81a) and (81b) comprises an oscillator (30a) and output transistors (30b), which are alternately switched by the oscillator, allowing current to flow through the excitation windings (10c) and (20c) in alternating directions at the oscillator frequency. The load of the output transistors is set to allow the current to drive each toroid into magnetic saturation at the peak current values in both directions. The amplifiers (12) and (22) and integrators (14) and (24) receive the voltage developed across their respective detection windings (10b) and (20b) when the toroid is driven into and out of saturation, and then provide an integrated voltage which is proportional to any external static magnetic field flux passing through the toroid on an axis parallel to the winding axis of the detection windings. The amplifiers (12) and (22) are biased to remain within their dynamic range during operation of the detection apparatus, and to account for slight variations in the flux-gate toroidal sensors (81a) and (81b).

The differential amplifier (40) amplifies the difference between the integrated voltages from the integrators. The magnitude circuit (60) provides a voltage proportional to the magnitude of this difference voltage, and a polarity voltage coding the polarity of the difference voltage.

The visual display driver (62) includes an integrated circuit which drives a visual display (66), such as a 10-step light emitting diode bar array, depending on its input voltage. A polarity circuit (70) and a polarity display driver (72) drive one of two light emitting diodes (74a) and (74b), depending on the polarity voltage. A voltage-controlled oscillator chip generates a speaker-projected sound whose pitch is proportional to the input voltage. The 10-step bar array displays the magnitude of the magnetic field gradient detected by the flux-gate toroidal sensors, while one of the two light emitting diodes lights up to indicate the polarity of the gradient.

Example 2

Detection of a Feeding Tube

Figure 4:
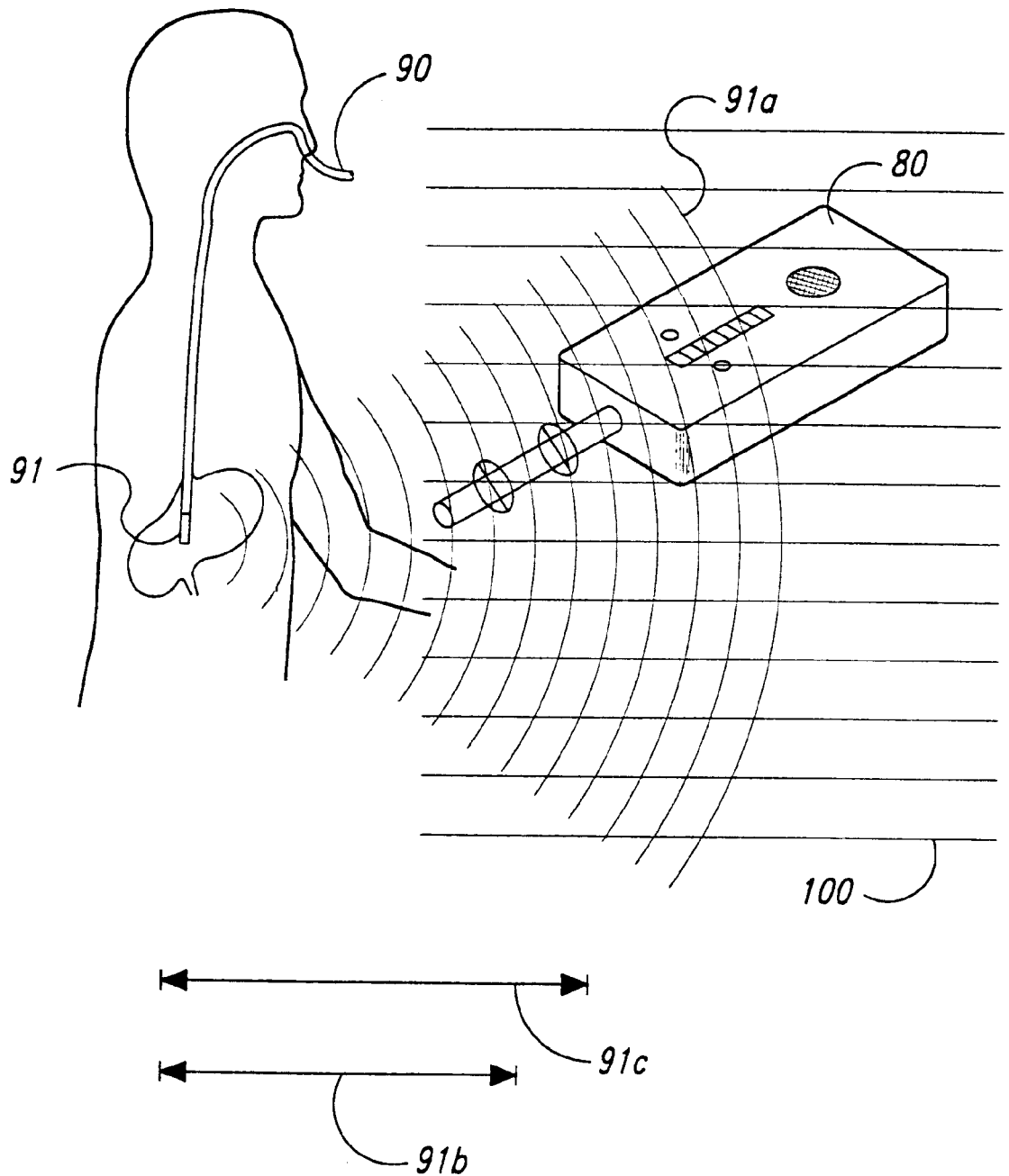
FIG. 4 illustrates the location of a magnet fixed to the end of a medical tube positioned within the body of a human patient using the detection apparatus of FIG. 3.

Referring to FIG. 4, a feeding tube (90), with a permanent magnet (91) located in its tip, includes an elongated, tubular, main portion with a sealed magnet chamber at its distal end, and an adapter at its proximal end to allow connection to a source of feeding formula. Side apertures at the distal end, above the magnet chamber, extend from the inner tube lumen to the exterior of the tube allowing the feeding formula to reach the patient's stomach. The sealed magnet chamber contains a cylindrical, rare earth, permanent magnet (91), of approximate size 0.10 inches diameter by 0.50 inches in length. The chamber is fused to the distal end of the feeding tube with its long axis parallel to the long axis of the feeding tube. The feeding tube and magnet chamber are composed of a flexible polymer which is chemically, biologically, and mechanically appropriate for purposes of gastroenteric feeding.

The feeding tube (90) is inserted into a patient's nose, down the esophagus and into the stomach. The detection apparatus (80) described in Example 1 above and illustrated in FIG. 3, is used to sense the magnet's static magnetic field strength (91a) at two different distances (91b) and (91c) while immersed in the earth's ambient magnetic field (100). As the detection apparatus (80) is moved about the patient's body, greater and lesser magnetic field gradients are indicated. The feeding tube (90) is located by moving the detection apparatus until the greatest magnitude is indicated by detection apparatus (80).

Example 3

Detection Apparatus

Figure 5:
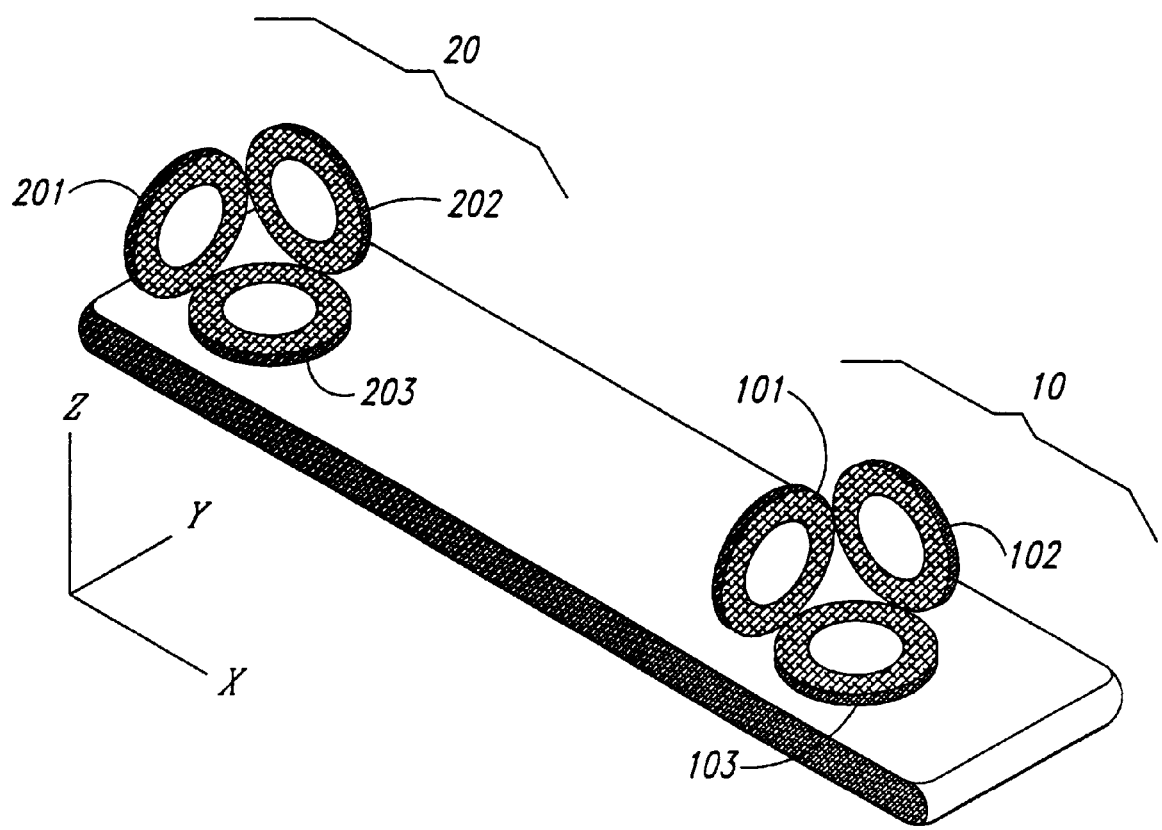
FIG. 5 illustrates the orientation of the x, y and z flux-gate sensors in an embodiment of a detection apparatus of this invention.

Referring to FIG. 5, in a preferred alternative embodiment of the apparatus of Example 1, the first sensor (10) includes x, y, and z-axis sensors (101), (102), and (103), respectively, while the second sensor (20) includes x, y, and z-axis sensors (201), (202), and (203), respectively. In this embodiment, the sensors are flux-gate toroidal sensors with an associated sensor driver (not shown).

Figure 6:
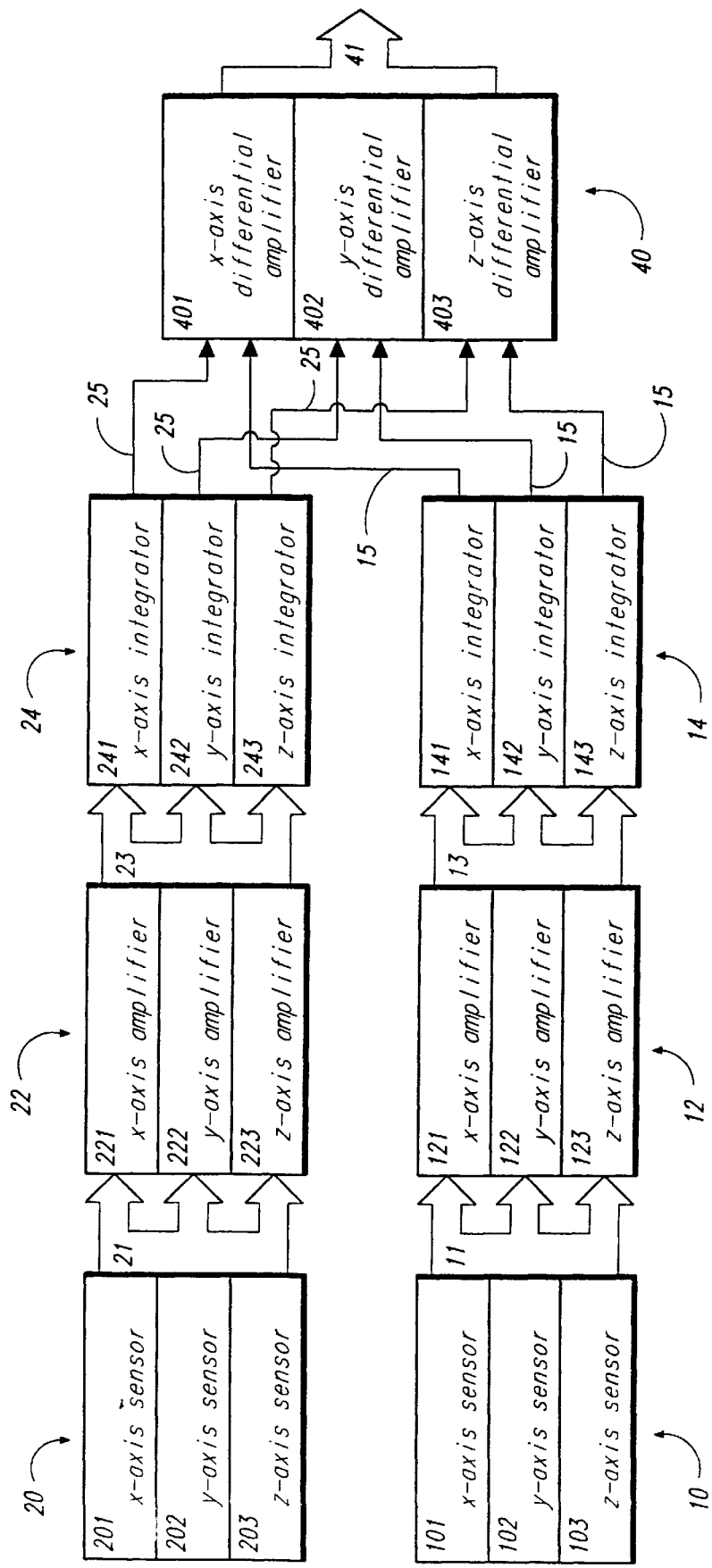
FIG. 6 is a block diagram illustrating the structure and operation of a preferred embodiment of the detection apparatus of FIG. 1A.

Referring to FIG. 6, the first and second sensor signals (11) and (21), the first and second amplified signals (13) and (23), the first and second detection signals (15) and (25), and the differential signal (41) are vectors.

The first amplifier (12) includes x, y, and z-axis amplifiers (121), (122) and (123). Similarly, the second amplifier includes x, y, and z-axis amplifiers (221), (222) and (223). In addition, the first integrator (14) includes x, y, and z-axis integrators (141), (142) and (143), while the second integrator includes x, y, and z-axis integrators (241), (242) and (243). Finally, the differential amplifier (40) includes x, y, and z-axis differential amplifiers (401), (402) and (403).

The operation of the first and second sensors (10) and (20), the first and second amplifiers (12) and (22), the first and second integrators (14) and (24), and the differential amplifier (4), is the same as in Example 1, with the exception that in this preferred embodiment, the signals (11), (21), (13), (23), (15), (25), and (41) are vectors.

Example 4

Detection Apparatus with Wound-Core Inductive Sensors

As noted above, the invention may be implemented with analog, mixed-mode, or digital elements. In a preferred embodiment, the detection apparatus detects the static magnetic field strength gradient as a vector, as opposed to a scalar.

Figure 7:
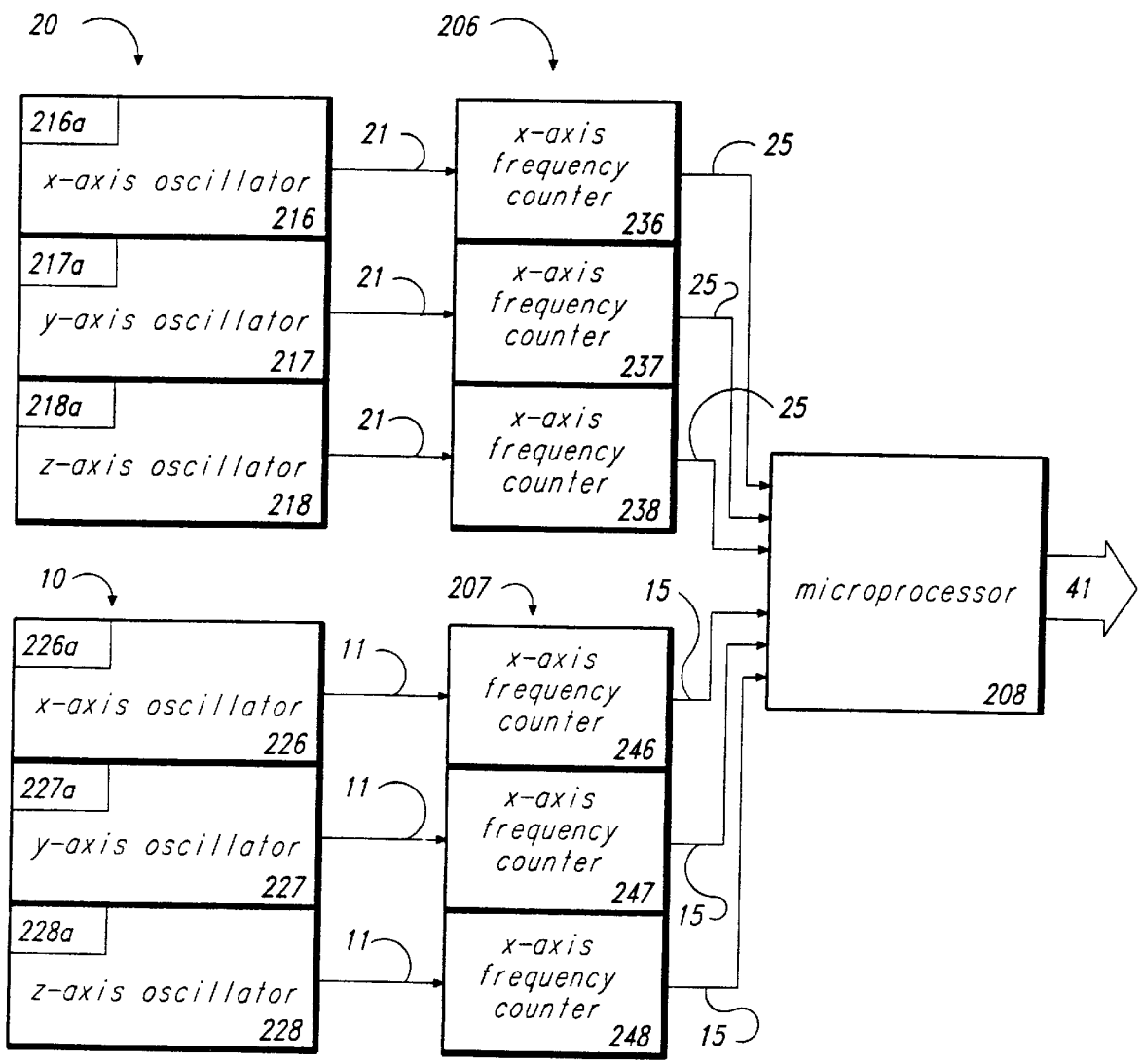
FIG. 7 is a block diagram illustrating a preferred embodiment of a detection apparatus of this invention comprising first and second sensors, first and second detectors, and a microprocessor.

Referring to FIG. 7, a representative embodiment includes a first and second sensor (10) and (20), a first and second detector (207) and (206), and a microprocessor (208).

The first sensor (10) includes an x, y, and z-axis oscillator (226), (227) and (228) having associated wound-core inductive sensors (226a), (227a) and (228a), respectively. Similarly, the second sensor (20) includes an x, y, and z-axis oscillator (216), (217) and (218) having wound-core inductive sensors (216a), (217a) and (218a), respectively. Further, the first detector (207) includes an x, y, and z-axis frequency counter (246), (247) and (248), while the second detector (206) includes an x, y, and z-axis frequency counter (236), (237) and (238).

The first and second sensor signals (11) and (21), the first and second detection signals (15) and (25), and the differential signal (41) are vectors. The first sensor x, y, and z-axis oscillators provide the x, y, and z components, respectively, of the first sensor signal (11). Similarly, the first detector x, y, and z-axis frequency counters provide the x, y, and z components, respectively, of the first detection signal (15). Likewise, the second sensor x, y, and z-axis oscillators provide the x, y, and z components, respectively, of the second sensor signal (21), and the second detector x, y, and z-axis frequency counters provide the x, y, and z components, respectively, of the second detection signal (25).

The wound-core inductive sensors (216a), (217a), (218a), (226a), (227a), and (228a) are high-permeability magnetic cores wrapped with windings. Each wound-core inductive sensor, together with its associated oscillator, comprises an LR relaxation oscillator having a period fixed by the inductance L of the sensor. Since the inductance L of each sensor is a function of the static magnetic field strength sensed by that sensor, the period of the associated oscillator is a function of the same static magnetic field strength.

Thus, the x, y, and z-axis frequency counters (246), (247) and (248) receive the x, y, and z components, respectively, of the first sensor signal (11), and the period of these components is a function of the first static magnetic field strength. Similarly, the x, y, and z-axis frequency counters (236), (237) and (238) receive the x, y, and z components, respectively, of the second sensor signal (21), and the period of these components is a function of the second static magnetic field strength.

Each frequency counter determines the frequency of its associated first or second signal component. It then provides that frequency to the microprocessor (208) in the form of the first and second detection signals (15) and (25). The microprocessor (208) determines the magnitude of the detection signals (15) and (25) by subtracting the second detection signal vector from the first detection signal vector, summing the squares of the components of the resulting difference vector, and taking the square root of the resulting sum. The microprocessor then provides the differential signal (41) to the magnitude circuit.

From the foregoing, it will be appreciated that, although specific embodiments of this invention have been described herein for purposes of illustration, various modifications may be made without deviating from the spirit and scope of the invention. Accordingly, the invention is not limited except by the appended claims.

We claim:

1. A system for detecting the location of a medical tube within a patient comprising: a detection apparatus and a medical tube, wherein the medical tube comprises a tube or device suitable for insertion into the patient's body and a permanent magnet associated with the medical tube, the medical tube having a proximal end and distal end, and the permanent magnet generating a static magnetic field of sufficient strength per unit volume to permit detection by the detection apparatus of the magnet's static magnetic field when the medical tube is inserted into the patient's body, and wherein the magnet is associated with the distal end of the medical tube in a fixed orientation with a magnetic dipole pointing to the proximal end and parallel to a longitudinal axis of the medical tube such that polarity of the magnet's static magnetic field as sensed by the detection apparatus indicates the orientation of the distal end of the medical tube within the patient's body, and wherein the medical tube is selected from the group consisting of a catheter and medical instrument, and wherein the detection apparatus comprises first and second magnetic field strength sensors for sensing magnetic field strength and providing first and second magnetic field strength signals, a sensor driver for providing a driver signal to said first and second magnetic field strength sensors configured geometrically to null detection of ambient homogeneous magnetic fields to a value of zero, and a visual display or speaker operatively connected to the first and second magnetic field strength sensors for allowing visual or audible indication of said first and second magnetic field strength signals received therefrom.

2. The medical tube of claim 1 wherein the magnet is permanently affixed to the medical tube.

3. The medical tube of claim 1 wherein the magnet is removably affixed to the medical tube.

4. The medical tube of claim 1 wherein the catheter is selected from the group consisting of a feeding tube, urinary catheter, dilating catheter, pH catheter and motility catheter.

5. The medical tube of claim 1 wherein the catheter is a feeding tube.

6. The feeding tube of claim 5 having a tip end, wherein the magnet is incorporated in the tip end of the feeding tube.

7. The medical tube of claim 1 wherein the catheter is selected from the group consisting of a nasogastric tube, endotracheal tube, stomach pump tube, wound drain tube, rectal tube, vascular tube, Sengstaken-Blakemore tube, colonic decompression tube and urological tube.

8. The medical tube of claim 1 wherein the medical instrument is selected from the group consisting of an endoscope and a colonscope.

* * * * *